United States Patent [19]

Donato

[11] Patent Number: 4,598,416
[45] Date of Patent: Jul. 1, 1986

[54] FILM HOLDER & BITE BLOCK DEVICE FOR RADIOGRAPHING TEETH DURING ENDODONTIC TREATMENT

[76] Inventor: Dominic A. Donato, 1340 Summit La., Mountainside, N.J. 07092

[21] Appl. No.: 639,744

[22] Filed: Aug. 13, 1984

[51] Int. Cl.⁴ .......................... A61B 6/14; G03B 42/04
[52] U.S. Cl. ..................................... 378/168; 378/170
[58] Field of Search ................................. 378/170, 168

[56] References Cited

U.S. PATENT DOCUMENTS

| | | | |
|---|---|---|---|
| 1,608,269 | 11/1926 | Freund | 378/170 |
| 3,003,062 | 10/1961 | Updegrave | 378/170 |
| 3,473,026 | 10/1969 | Updegrave | 378/170 |
| 3,936,643 | 2/1976 | Toner | 378/168 |

Primary Examiner—Craig E. Church
Assistant Examiner—Jack I. Berman

[57] ABSTRACT

A device which aligns X-ray beam to the film at a predetermined vertical angle and a predetermined horizontal angle simultaneously. The specific angles are created by setting the angle indicating arrows to the appropriate angle on the vertical and horizontal scales. This non-parallel plane alignment of beam to film creates the desired image distortion predicted by the buccal object rule and often necessary in the practice of endodontics. The bite block and film holding arm portions are arranged in an off-set manner to allow for radiographing of teeth with endodontic files protruding from them. In addition, the bite block, by means of attached trays filled with dental impression material, e.g. compound, can register a biting position of the jaws. In any successive film exposure, the radiographic view of the original exposure can be duplicated by keying the teeth to the impressed material and re-setting the original horizontal and vertical angles.

4 Claims, 8 Drawing Figures

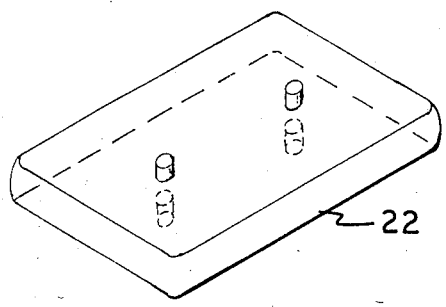
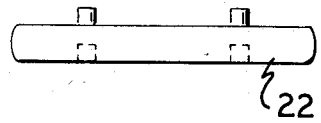
FIG. 5
FIG. 6
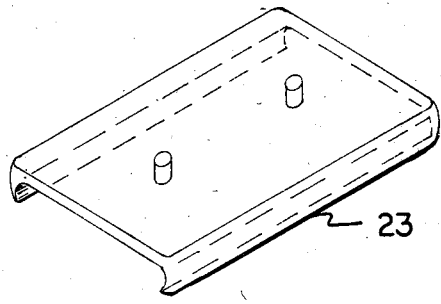
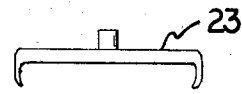
FIG. 7
FIG. 8

FILM HOLDER & BITE BLOCK DEVICE FOR RADIOGRAPHING TEETH DURING ENDODONTIC TREATMENT

This invention is a significant improvement of the XCP (extension cone paralleling) instrument produced by the Rinn Corp. The invention improves and differs from the XCP instrument in the following ways: first, there can be angular movement of the X-ray cone positioning ring with respect to the film holding arm in both the vertical and horizontal planes simultaneously. This permits the X-ray beam to strike the film at an angle, rather than being limited to parallel plane alignment (i.e. 0 degrees). Second, the degree of horizontal angulation of X-ray beam to film can be measured and read on a scale. Third, the degree of vertical angulation of X-ray beam to film can be measured and read on a scale. Fourth, it allows a radiograph to be taken of a tooth with an endodontic file protruding from it. This can be accomplished because the film holding arm and bite block are off-set with respect to each other and sufficient space is created between the jaws by snapping on additional blocks to the bits block and thus increasing its thickness. The XCP instrument (Rinn Corp.) cannot be used when endodontic files are protruding from the tooth because of the "L" shaped manner in which the film holding portion and bite block are attached, and because of the insufiicient, invariable thickness of the bite block. Fifth, it allows for duplication of a particular radiographic view of a tooth or other structure. The bite block contains a removable tray which can retain dental impression material. A second tray, also from retaining dental impression material, is attached to the bottom of the bite block or snapped on to the additional blocks. The bite block film holder complex is secured to the off-set rigid arm. The patient is instructed to bite on the bite block, and by so doing, impresses his teeth into the material contained in the upper and lower trays attached to the bite block. Now, the bite block film holder complex, and hence the film, can be keyed to this position in successive radiographic exposures. Once reseated in this keyed position and the original horizontal and vertical angles re-set, the particular radiographic view of a tooth or structure previosuly radiographed can be duplicated.

The view duplication feature, an object of this invention, is very useful in many areas of dentistry. It makes it possible to observe radiographic changes of a structure over time. If the same view of the structure is not maintained in each radiograph, then the changes observed may be an artifact of the positioning of the beam, film and object. The radiographic view must remain constant in each exposure if the variability of view is to be eliminated as a possible reason for the radiographic changes observed. In the field of diagnosis the observed object may be a suspected tumor or carious lesion. In research, the observed object may be hard structures of either animal or human. In periodontics, it may be an infrabony pocket, while in endodontics the observed object may be a periapical radiolucency. These are only a few examples in which radiographic view duplication is valuable.

Another object of this invention is to allow the taking of a radiograph of a tooth which is being endodontically treated. In conventional endodontic treatment an instrument (file) is placed within the pulp of the tooth. Since the file protrudes beyond the occlusal surface of the tooth, it is impossible to have the patient bite on bite block of an XCP holder (Rinn Corp.) in an attempt to radiograph the tooth and file. By significantly changing the design and improving the bite block, this problem is curcumvented. By attaching the film holding arm and bite block in an off-set manner and providing additional snap-on blocks to increase the height of the bite block, the patient can hold the bits block between his teeth anterior (or lateral in the case of treating anterior teeth) to the tooth being treated. The off-set configuration allows the file to protrude unobstructed by the bite block, and the additional blocks keep the patient's mouth opened wide enough to prevent the opposite dental arch from contacting and disturbing the file.

In endodontic treatment, it is necessary to create controlled radiographic image distortion to gain a clearer view of overlapping roots, canals or etc. The buccal object rule predicts the distortion caused by varying the angle with which the beam strikes the film. It is an object of this invention to allow the practitioner to read on a scale and record the beam to film angles (horizontal and vertical) which created a specific image distortion on the resultant radiograph. He can then alter these angles in a controlled manner in successive exposures if he deems it necessary to change the distortion pattern, or he can maintain the same angles to reproduce the same degree of distortion.

IN THE DRAWINGS

Figure 4:
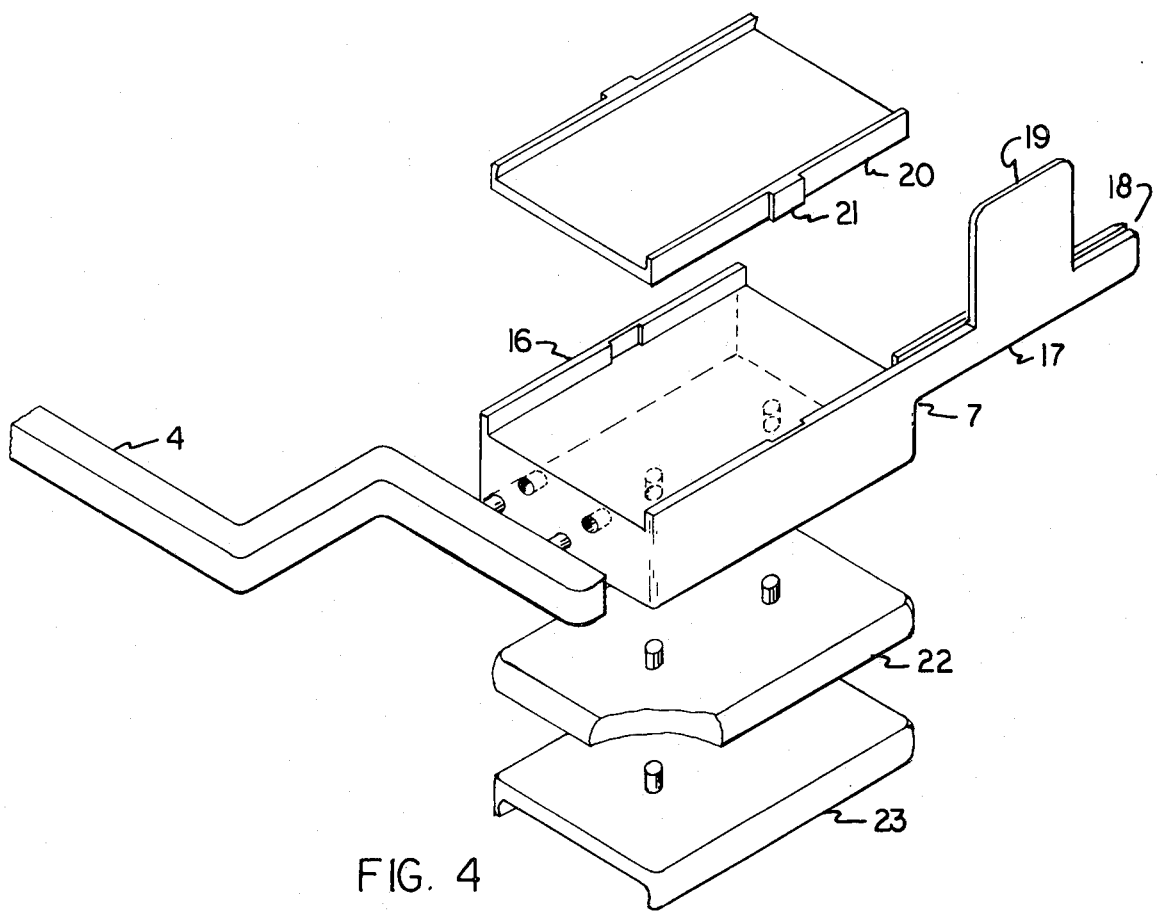

FIG. 4 is an exploded isometric view of top and back of film holder - bite block complex. Also shown is a single snap-on extension block and the snap-on tray. Part of the attachment arm for the bite block is shown for completeness.

FIG. 5 is an isometric viewe of an additional (snap-on) block 22.

FIG. 6 is a side view of an additional (snap-on) block 22.

FIG. 7 is an isometric view of the attachable bottom tray 23.

FIG. 8 is an end view of the attachable bottom tray 23.

Figure 1:
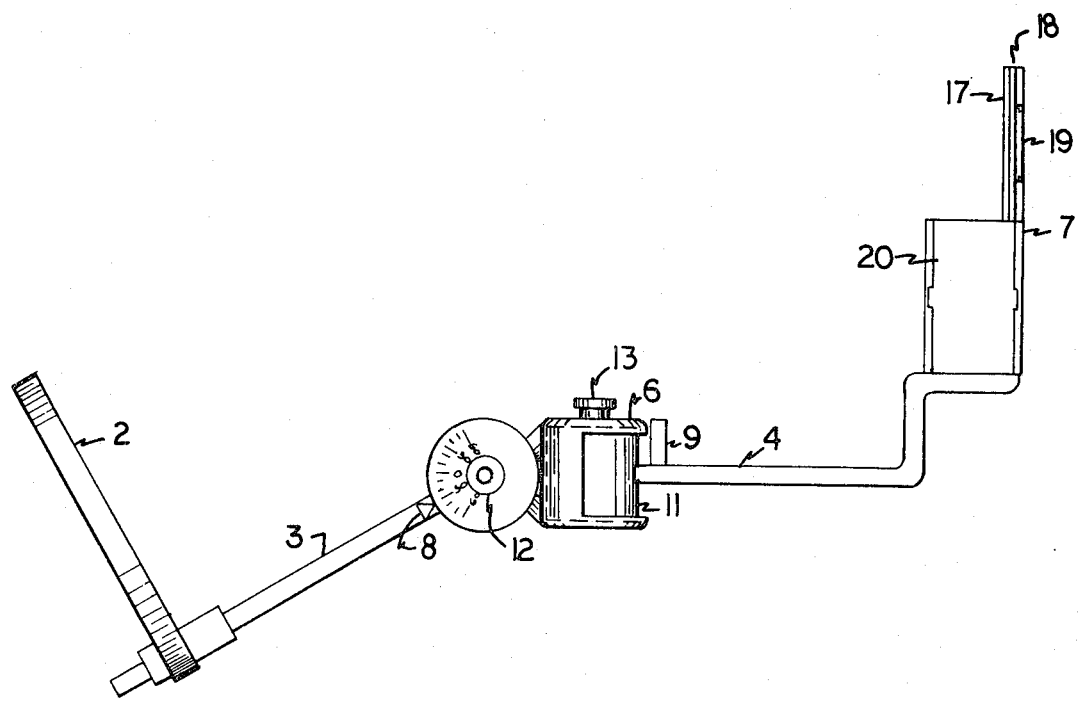
FIG. 1 is a top plan view of the invention with the x-ray beam to film alignment having a positive horizontal angulation.

Referring to FIG. 1, there is illustrated a film to beam angular aligning device 1, that consists of a rotatable arm 3. The arm 3 rotates in the horizontal plane by means of a joint consisting of the stationary housing 5 which contains the movable inner cylindrical core. This inner core is rigidly fixed to the arm 3 and is attached to the housing 5 by means of a bolt and nut 12.

There is a ring 2 to which the long cone of the x-ray machine is aligned and the ring 2 can slide on the arm 3.

The outer surface of the housing 5 is imprinted with angular gradations which in combination with the indicator arm 8, rigidly fixed to arm 3, indicates the degree of horizontal angulation the x-ray cone will have with respect to the film.

The arm 4 is rigidly attached to the inner core 11, which is contained by the housing 6. A bolt and nut 13 attach the core to the housing. The housing 6 is rigidly attached to the housing 5, and consequently, when arm 4 is held stationary, housing 6, and all parts attached to it, including ring 2, will rotate in the vertical plane. This accomplishes the vertical angulation of the x-ray cone to the film.

The outer surface of the housing 6 is imprinted with angular gradations which in combination with indicator arm 9, rigidly fixed to arm 4, indicates the degree of vertical angulation of the x-ray cone to film.

Bite block-film holder complex 7 consists of bite block 16 and film holding arm 17. The complex 7 is detachable from arm 4. Bite block 16 is held by the patient between his upper and lower teeth while the film is placed into the film holder 17 which consists of a groove 18 and a support panel 19. Bite block 16 consists of a removable top panel 20 which can be inverted and reinserted to serve as a tray for dental impression materials, e.g. compound.

Figure 2:
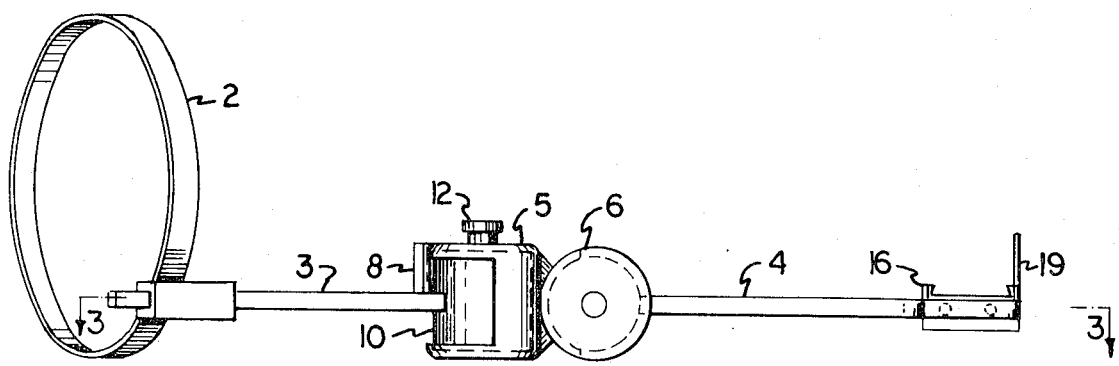
FIG. 2 is a side elevtional view with the vertical plane alignment of beam to film to at 0 degrees.

FIG. 2 is a side elevational view of device 1 shown in FIG. 1. The rotating core 10 rigidly fixed to arm 3 is shown in FIG. 2.

Figure 3:
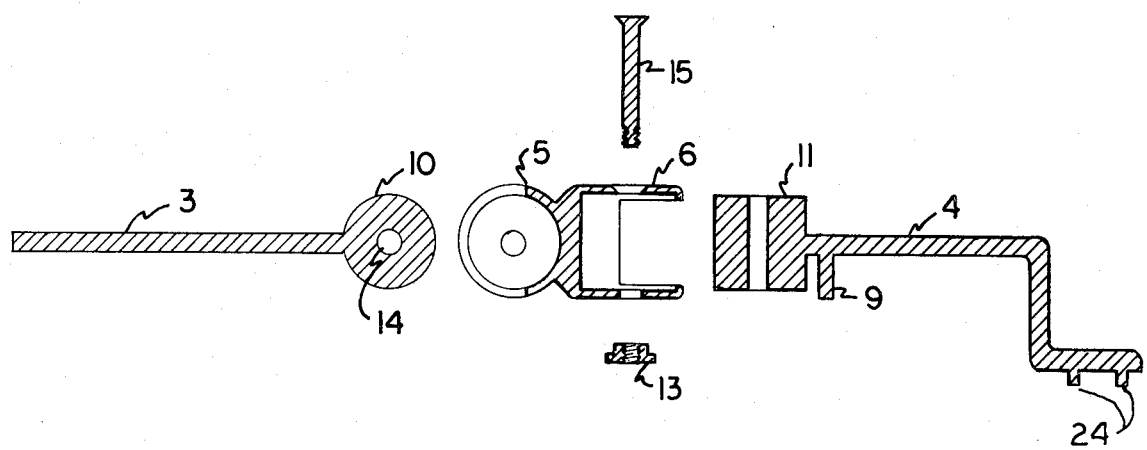
FIG. 3 is an exploded longitudinal cross-sectional view taken substantially along line 3—3 of FIG. 2 rotated 90 degrees. The positioning ring and bite block have been removed for clarity.

FIG. 3 is an exploded longitudinal cross-sectional view of FIG. 2 rotated 90 degrees taken substantially along line 3—3. The bite block-film holder complex 7 and the ring 2 are removed for clarity. The cross-sectional view of bolt 14 is shown. Bolt 14, together with nut 12 shown in FIG. 1, attach the core 10 to the housing 5, and acts as an axle allowing the core 10, with attached arm 3, to rotate within the housing 5 in the horizontal plane.

The bolt 15, together with nut 13, attaches the core 11 to the housing 6. When the device is held between the teeth by means of the bite block, the housing 6 and all parts attached to it, can rotate around core 11, providing rotation in the vertical plane.

Nubs 24 are a part of arm 4 and fit into mated sleeves in the bite block. This allows for the attachment of the bite block - film holding complex to arm 4.

FIG. 4 is an exploded isometric view showing the top and back of the film holder-bite block complex 7. The film holding portion 17 consists of an arm with an inscribed groove 18 and a support panel 19. a dental x-ray film packet is placed into the groove 18, and is supported by the back panel 19. The bite block portion 16 which contains sleeves for attachment of the complex 7 to arm 4 (male-female type of interlock) provides a biting surface which allows the patient to grip the device between his upper and lower teeth. There is a removable insert 20 in the top of the bite block 16 which can serve as a solid top surface for biting or, when removed, inverted, and replaced back into the bite block functions as a tray for impression material e.g. dental compound. The internal surfaces of the two parallel sides of tray 20 are slightly convergent to aid in the retention of the impression material. This reversible tray insert 20 is secured in a definite position in the bite block 16 by means of nubs and associated key-ways. A slot or key-way is located on each side of the concavity of the bite block. One of the keyed nubs is designated 21 in FIG. 4.

Additional solid blocks can be attched to the bottom of bits block 16 in order to increase its overall thickness and hence allow for a greater opening of the patient's jaws. One such additional block 22 is shown in FIG. 4. But more than one block can be added by simply attaching several blocks together by means of a male - female type of peg interlock. The thickness of each additional block can vary, but otherwise their forms are identical.

A tray 23 can be attached to the bottom of bite block 16 or to any of the additional blocks 22. The tray 23 can be filled with dental impression material e.g. dental compound. The internal surfaces of the two parallel sides of the tray 23 are slightly convergent to aid in the retention of the impression material.

FIG. 5 shows the top view of an additional solid bodied block 22.

FIG. 6 shows the bottom view of an additional block 22.

FIG. 7 shows the isometric view of the attachable bottom tray 23.

FIG. 8 shows the top view of the attachable tray 23.

The foregoing description and the drawings are given merely to explain and illustrate the invention and the invention is not to be limited thereto, except insofar as the appended claims are so limited, since those skilled in the art who have the disclosure before them will be able to make modifications and variations therein without departing from the scope of the invention.

I claim:

1. A bite block-film holder complex in which the bite block is laterally affixed as viewed from the x-ray source to the film holder portion to allow instruments, e.g. endodontic files, to protrude from the object tooth in an unobstructed manner.

2. A bite block-film holder complex as in claim 1, wherein the thickness of the bite block portion is adjustable, and said ajdustment is accomplished by attaching blocks to said bite block.

3. A bite block-film holder complex as in claim 2, wherein a tray for impression material, or any other material, can be attached to the bottom of the said bite block or any added block.

4. A bite block-film holder complex in which the top panel of the bite block is removalbe and, when inverted, can be replaced into the bite block and serve as a tray for impression materials or any other material.

* * * * *